United States Patent [19]

Russell et al.

[11] Patent Number: 4,979,714
[45] Date of Patent: Dec. 25, 1990

[54] DRAINAGE BAG HANGER

[75] Inventors: John P. Russell, Centerpoint; Terry Carroll, Dora, both of Ala.

[73] Assignee: Infection Control Products, Inc., Gardendale, Ala.

[21] Appl. No.: 417,585

[22] Filed: Oct. 5, 1989

[51] Int. Cl.⁵ .............................................. A47H 1/16
[52] U.S. Cl. ........................................ 248/303; 24/716
[58] Field of Search ............... 248/303, 302, 211, 213, 248/214, 215, 304; 211/119; 24/555, 559, 237, 230.5 R, 230.5 AD, 230.5 W, 230.5 TP, 320

[56] References Cited

U.S. PATENT DOCUMENTS

| | | | |
|---|---|---|---|
| 595,693 | 12/1897 | Cameron | 24/230.5 W |
| 823,317 | 6/1906 | Best | 24/710.9 |
| 932,778 | 8/1909 | Gould | |
| 1,277,483 | 9/1918 | Rogers | |
| 2,244,572 | 6/1941 | Rawlins | 24/230.5 AD |
| 2,503,108 | 4/1950 | Glandville | 248/303 |
| 2,584,194 | 2/1952 | Drury | 24/555 X |
| 2,839,803 | 6/1958 | Wiselka | 24/230.5 AD |
| 3,074,451 | 12/1963 | Whitney | 150/1 |
| 3,155,298 | 11/1964 | Brown | 224/5 |
| 3,231,901 | 2/1966 | Kennedy | 4/110 |
| 3,777,697 | 12/1973 | Woessner | 116/118 R |
| 3,963,156 | 6/1976 | Perrin | 224/1 R |
| 4,027,842 | 6/1977 | Mittleman | 248/75 |
| 4,312,352 | 1/1982 | Meisch et al. | 128/294 |
| 4,358,036 | 11/1982 | Maltais | 224/252 |
| 4,475,676 | 10/1984 | Smith | 224/247 |
| 4,684,367 | 8/1987 | Schaffer et al. | 604/140 |
| 4,887,785 | 12/1989 | Blaich | 248/339 |

Primary Examiner—J. Franklin Foss
Attorney, Agent, or Firm—George A. Bode; Michael L. Hoelter

[57] ABSTRACT

A hanger clip in the shape of a closed "S" having coplanar, symmetrical loops. The end portions of the hanger clip are bent at their termini at an approximately ninety (90°) degree angle with the vertices of these forming approximately ninety (90°) degree angles and being located adjacent the mid-region of the hanger clip.

16 Claims, 3 Drawing Sheets

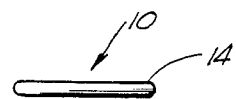
FIG. 4
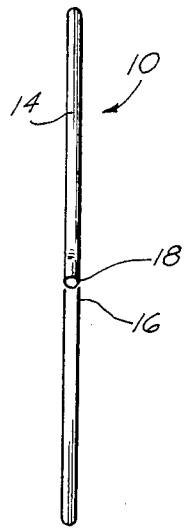
FIG. 2
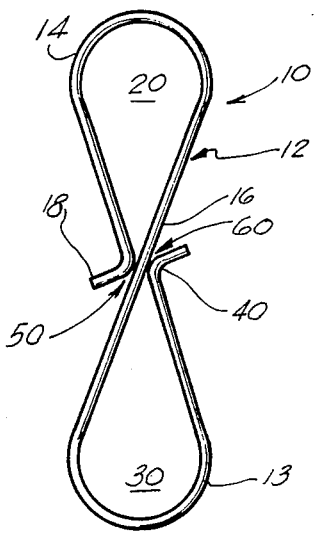
FIG. 1
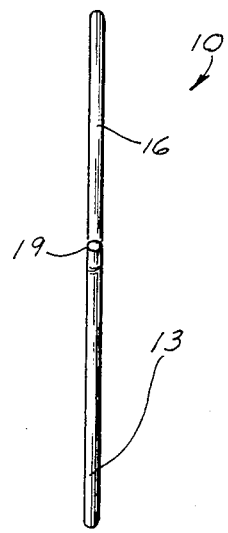
FIG. 3
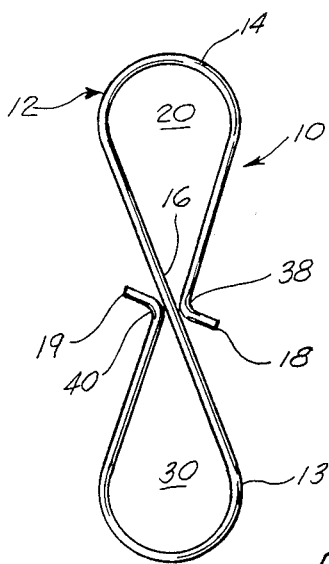
FIG. 5
FIG. 6
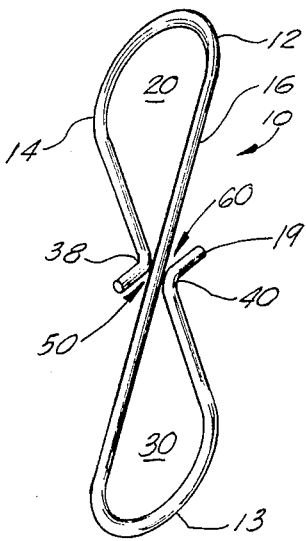
FIG. 7

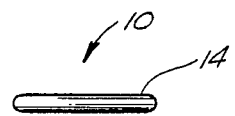
FIG. 11
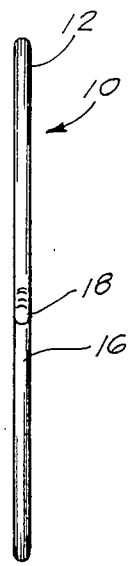
FIG. 9
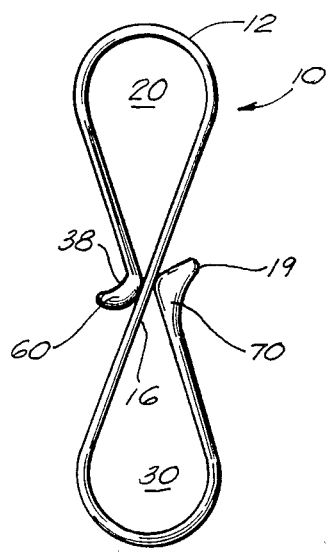
FIG. 8
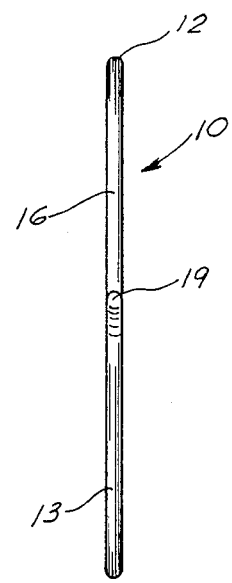
FIG. 10
FIG. 12
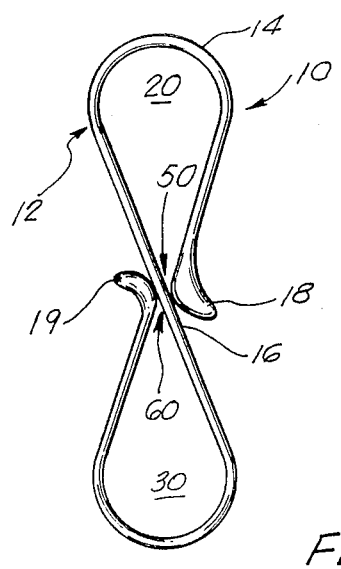
FIG. 13
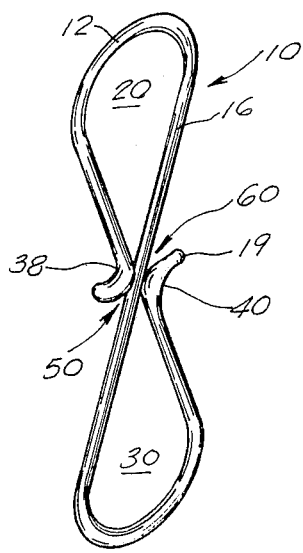
FIG. 14

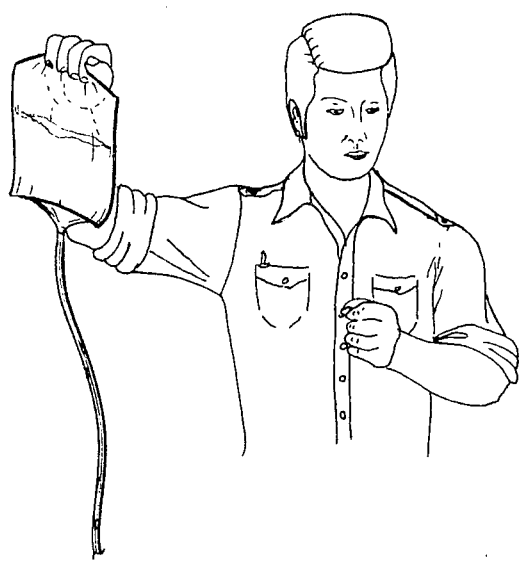
PRIOR ART
FIG. 15
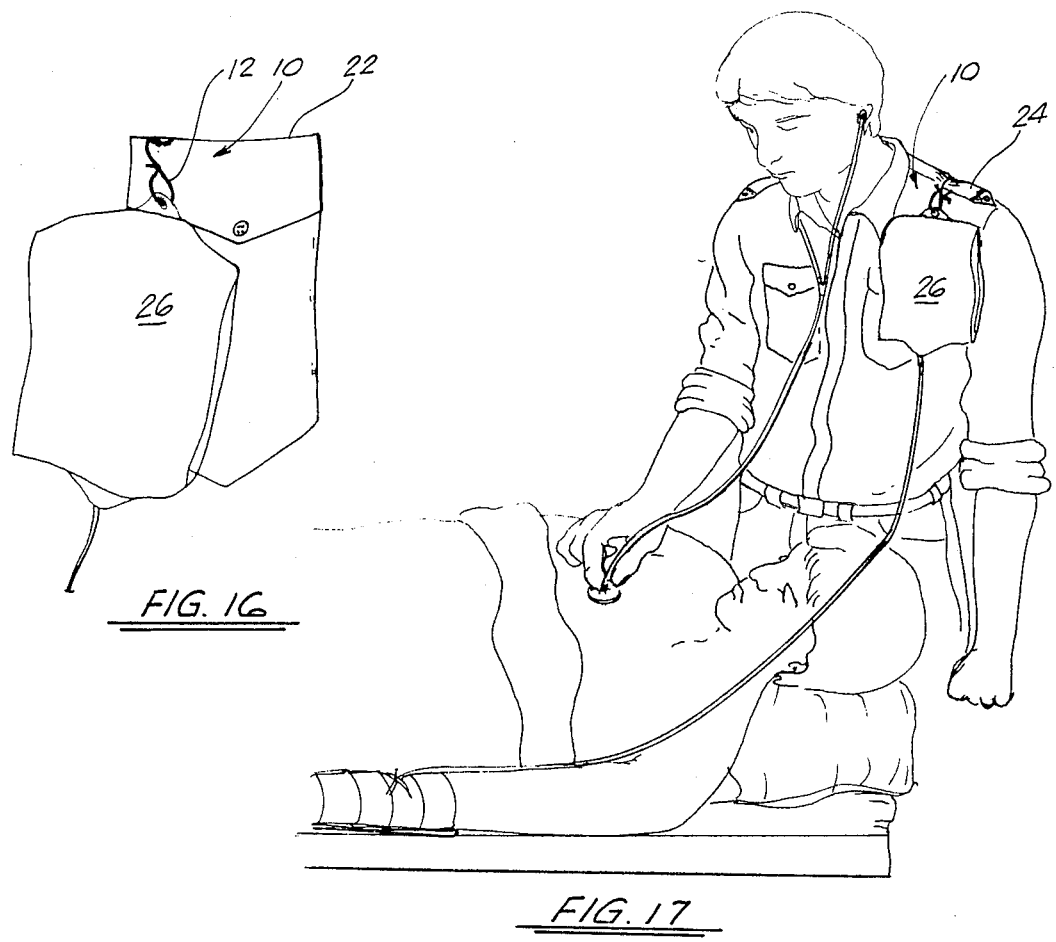
FIG. 16
FIG. 17

DRAINAGE BAG HANGER

BACKGROUND OF THE INVENTION

1. Field of the Invention

This invention pertains to clips or hooks or hangers in general and, more particularly, to a clip for hanging a drainage bag, such as an intravenous ("I.V.") bag, therefrom.

2. General Background

In the medical arts, drainage bags such as I.V. bags are very common and well known. To work properly, they must be supported above the body of the patient so that gravity will induce the fluid to flow. In hospitals and other controlled areas, supporting the bag above the body is not a difficult procedure, but in emergency situations occurring outside the hospital setting, maintaining the proper elevation of an I.V. bag can hinder patient assistance. This is because oftentimes one person, such as a paramedic, must elevate the bag with one hand while attempting to render assistance with the other. In other cases, the paramedic might lay the bag on the ground and kneel on it to apply the needed pressure (with the attendant danger of excessive pressure and I.V. flow). In other cases, the paramedic might hold the bag in his or her mouth which is unsanitary, unstable and effectively eliminates any communication with another person.

It is thus an object of this invention to provide a hanger clip that is safe, easy to use, and effective, particularly with I.V. bags. Another object of this invention is to provide a hanger clip that can support a drainage bag from the clothes or pockets of a user. Still another object of this invention is to provide a hanger clip that can easily be hooked or unhooked from the bag or from the user as needed. A further object of this invention is to provide a hanger clip that can be used in a variety of situations and can attach to a variety of supports as needed. These and other objects of this invention will become obvious upon further investigation.

SUMMARY OF THE PRESENT INVENTION

The preferred embodiment of the apparatus of the present invention solves the aforementioned problems in a straightforward and simple manner. What is provided is a hanger clip for suspending a fluid bag, such as an I.V. bag, therefrom comprising an elongated stiff wire defined by a mid-region and two (2) end regions, the end regions are folded back, thereby forming a pair of opposing loops. These loops are co-planar and are symmetrically located on opposing sides of the midregion of the wire (the wire is bent in opposite directions). Additionally, the terminus of each end region are bent at an approximately ninety (90°) degree bend. The vertex of each of these ninety (90°) degree bends is adjacent but spaced from the mid-region and it is between these vertices and the mid-region that access to the loops is provided.

BRIEF DESCRIPTION OF THE DRAWINGS

For a further understanding of the nature and objects of the present invention, reference should be had to the following description taken in conjunction with the accompanying drawings in which like parts are given like reference-numerals and, wherein:

FIG. 1 is a front elevational view of the preferred embodiment of the apparatus of the present invention;

FIG. 2 is a left side elevational view of the embodiment of FIG. 1;

FIG. 3 is a right side elevational view of the embodiment of FIG. 1;

FIG. 4 is a top plan view of the embodiment of FIG. 1;

FIG. 5 is a bottom plan view of the embodiment of FIG. 1;

FIG. 6 is a rear elevational view of the embodiment of FIG. 1;

FIG. 7 is a top perspective view of the embodiment of FIG. 1;

FIG. 8 is a front elevational view of another embodiment of the apparatus of the present invention;

FIG. 9 is a left side elevational view of the embodiment of FIG. 8;

FIG. 10 is a right side elevational view of the embodiment of FIG. 8;

FIG. 11 is a top plan view of the embodiment of FIG. 8;

FIG. 12 is a bottom plan view of the embodiment of FIG. 8;

FIG. 13 is a rear elevational view of the embodiment of FIG. 8;

FIG. 14 is a top perspective view of the embodiment of FIG. 8;

FIG. 15 is an illustrative view of one conventional (prior art) method of supporting an I.V. bag during use;

FIG. 16 is an illustrative view of the hanger clip of the present invention supporting an I.V. bag from a pocket; and, FIG. 17 is an illustrative view of the hanger clip of the present invention supporting an I.V. bag from an epaulet.

DETAILED DESCRIPTION OF THE PREFERRED EMBODIMENT

Referring now to the drawings, there is shown planar clip 10 preferably configured of a length of small diameter stiff wire 12. In length (not shown), wire 12 is comprised of integral first and second end portions 13, 14 and mid-region 16, and is bent into the shape of a closed "S" (FIGS. 6 and 13) with the end regions 13, 14 of wire 12 almost touching midregion 16 of wire 12 on opposing sides. As best seen in FIGS. 1, 6 and 7 and FIGS. 8, 13 and 14, end portions 13, 14 have terminating ends 18, 19 which are bent back to an angle of approximately ninety (90°) degrees creating vertices 38, 40 respectively, before teminating outwardly spaced a short distance (approximately one-quarter (¼") inch) from mid-region 16.

As thusly construed, the approximately 315° degree bending of end regions 13, 14 outlines loops 20, 30, best seen in FIGS. 1, 6 and 7 and 8, 13 and 14, that are teardrop in shape. Access to the interior of loops 20, 30 is made possible by the small gaps 50, 60 (on the order of about one-sixteenth (1/16") of an inch) between the vertices 38, 40 of end regions 14, 13, respectively, and mid-region 16. In both the embodiments of FIGS. 1-8 and FIGS. 9-14, loops 20, 30 and the bends in portions 13, 14 of wire 12 are co-planar, symmetrical, and have a tear-drop shape. In fact, they can be said to be a mirror image of each other occurring on opposite sides of the mid-point of mid-region 16 of wire 12. The symmetrical construction of clip 10 enables either loop 20 or 30 to be utilized as needed in an emergency situation without incurring any delay in determining the proper orientation of clip 10.

In this fashion, one end region 13 or 14 (and its associated vertex and terminating end) may be inserted through a buttonhole or around a piece of fabric or epaulet of a user so that the opposite loop 20 or 30, respectively, is available as a means for supporting or hanging an item, such as an I.V. bag, therefrom. The close proximity of vertices 38, 40 to mid-region 16 ensures that the item being hung will not come loose.

Loops 20, 30 are also sized and configured to enable a rod or other object to slide through it, thereby enabling the user to suspend the clip 10 from the rod and an object such as an I.V. bag from the remaining loop. Other embodiments of this planar clip include plastic construction or a rectangular or square cross-section. Also, flared end regions 13, 14 may be configured as shown in the second embodiment of FIGS. 8 through 14 with thicker, reinforced area 60, 70 around the ninety (90°) degree bend.

In use, as shown in FIGS. 16 and 17, one end of planar clip 10 is inserted into pocket 22 or around fabric or epaulet 24 so that fluid bag 26 can safely be suspended by the other end and thus from the user above the body of a patient for proper drainage.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A hanger for suspending a fluid drainage bag, or the like, therefrom comprising:
    (a) an elongated member having a mid-region and first and second end portions, said end portions being bent in opposing directions to form generally with said mid-region a pair of coplanar loops symmetrical about said mid-region; and,
    (b) each of said end portions having at its terminus a second bend therein, each of said second bends being in a direction opposite its first bend, the vertex of each of said second bends being adapted to engage said mid-region.

2. The apparatus of claim 1, wherein said second bends in the terminal of said end portions are outwardly of said mid-region at an angle of about ninety (99°) degrees.

3. The apparatus of claim 1, wherein said loops are tear-drop shaped.

4. The apparatus of claim 1, wherein said vertices have a cross-sectional area greater than that of said mid-region.

5. The apparatus of claim 4, wherein said bends in the termini of said end portions are outwardly of said mid-region at an angle of about ninety (90°) degrees.

6. The apparatus of claim 4, wherein said loops are tear-drop shaped.

7. A hanger for suspending a fluid drainage bag, or the like, therefrom comprising:
    (a) an elongated member having a mid-region and first and second end portions, said end portions being bent in opposing directions to form generally with said mid-region a pair of coplanar, nearly closed loops symmetrical about said mid-region; and,
    (b) each of said end portions having at its terminus a second bend therein, each of said second bends being in a direction opposite its first bend, the vertex of each of said second bends being adapted to engage said mid-region, thereby providing a means for engaging a fluid drainage bag to be supported therefrom.

8. The apparatus of claim 7, wherein said bends in the termini of said end portions are outwardly of said mid-region of an angle of about ninety (90°) degrees.

9. The apparatus of claim 7, wherein said vertices are on opposed sides of said mid-region of said elongated member.

10. The apparatus of claim 7, wherein said loops are tear-drop shaped.

11. The apparatus of claim 7, wherein said vertices have a cross-sectional area greater than that of said mid-region of said elongated member.

12. The apparatus of claim 11, wherein said bends in the termini of said end portions are outwardly of said mid-region at an angle of about ninety (90°) degrees.

13. The apparatus of claim 11, wherein said vertices are on opposed sides of said mid-region of said elongated member.

14. The apparatus of claim 11, wherein said loops are tear-drop shaped.

15. A hanger for suspending a fluid drainage bag, or the like, therefrom comprising:
    (a) an elongated member having a mid-region and first and second end portions, said end portions being bent in opposing directions to form generally with said mid-region a pair of coplanar, symmetrical nearly closed loops; and,
    (b) each of said end portions having at its terminus a second bend therein, each of said second bends being in a direction opposite its first bend, said bend being outwardly of said mid-region, the vertex of each of said second bends being adapted to engage said mid-region, thereby providing a means for engaging a fluid drainage bag to be supported therefrom.

16. The apparatus of claim 15, wherein said bends in the terminal of said end portions are outwardly of said mid-region at an angle of about ninety (90°) degrees.

* * * * *